United States Patent
Krishnan et al.

(10) Patent No.: US 9,803,207 B2
(45) Date of Patent: Oct. 31, 2017

(54) EXPRESSION VECTOR FOR PRODUCTION OF RECOMBINANT PROTEINS IN PROKARYOTIC HOST CELLS

(71) Applicant: BioGenomics Limited, West Thane, Maharashtra (IN)

(72) Inventors: Archana Krishnan, Maharashtra (IN); Sanjay Sonar, Maharashtra (IN); Damodar Thappa, Maharashtra (IN)

(73) Assignee: BIOGENOMICS LIMITED, West Thane, Maharashtra (IN)

( * ) Notice: Subject to any disclaimer, the term of this patent is extended or adjusted under 35 U.S.C. 154(b) by 0 days.

(21) Appl. No.: 14/908,791

(22) PCT Filed: Jul. 31, 2014

(86) PCT No.: PCT/IN2014/000504
§ 371 (c)(1),
(2) Date: Jan. 29, 2016

(87) PCT Pub. No.: WO2015/015516
PCT Pub. Date: Feb. 5, 2015

(65) Prior Publication Data
US 2016/0186190 A1  Jun. 30, 2016

(30) Foreign Application Priority Data
Jul. 31, 2013 (IN) .......................... 2526/MUM/2013

(51) Int. Cl.
*C12N 15/70* (2006.01)
(52) U.S. Cl.
CPC .................................. *C12N 15/70* (2013.01)

(58) Field of Classification Search
None
See application file for complete search history.

(56) References Cited

U.S. PATENT DOCUMENTS

2003/0104628 A1  6/2003  Hua et al.
2016/0168226 A1  6/2016  Krishnan et al.

FOREIGN PATENT DOCUMENTS

WO          01/73081 A1     10/2001
WO       2011/057237 A1      5/2011

OTHER PUBLICATIONS

International Search Report and Written Opinion from International Application No. PCT/IN2014/000504, dated Feb. 17, 2015.
J. W. Izard et al.: "Signal Peptides: Exquisitely Designed Transport Promoters", Molecular Microbiology, Wiley-Blackwell publishing LTD, GB, vol. 13, No. 5, Jan. 1, 1994 (Jan. 1, 1994), pp. 765-777, XP009041591.
Yogender Pal Khasa et al.: "Optimization of Human Granulocyte Macrophage-Colony Stimulating Factor (hGM-CSF) Expression Using Asparaginase and Xylanase Gene's Signal Sequences in *Escherichia coli*", Applied Biochemistry and Biotechnology, Part A: Enzyme Engineering and Biotechnology, Humana Press Inc, New York, vol. 165, No. 2, May 12, 2011 (May 12, 2011), pp. 523-537, XP019956391.

*Primary Examiner* — Nancy Treptow
(74) *Attorney, Agent, or Firm* — Merchant & Gould P.C.

(57) ABSTRACT

An expression vector for production of a recombinant protein in a host cell is provided. The expression vector includes a nucleotide sequence of Sequence ID No 2 encoding for a leader peptide of sequence ID No 3.

8 Claims, 3 Drawing Sheets

| Sr. No | Vectors | (GCSF - % expression) |
|---|---|---|
| 1 | GCSF expressed from control vector | Undetectable |
| 2 | GCSF expressed from pBG-BactX vector | 30.0 |

EXPRESSION VECTOR FOR PRODUCTION OF RECOMBINANT PROTEINS IN PROKARYOTIC HOST CELLS

This application is a National Stage Application of International Application No. PCT/IN2014/000504, filed 31 Jul. 2014, which claims benefit of Serial No. 2526/MUM/2013, filed 31 Jul. 2013 in India and which applications are incorporated herein by reference. To the extent appropriate, a claim of priority is made to each of the above disclosed applications.

FIELD OF THE INVENTION

The present invention relates to production of recombinant proteins in a host cell, and more particularly to an expression vector for production of recombinant proteins or their analogues in prokaryotic cells.

DESCRIPTION OF THE RELATED ART

Recombinant DNA (rDNA) technology has been used to clone, express and purify several proteins of therapeutic or other economic value from prokaryotic cells e.g., bacterial cells. The major advantages of producing recombinant proteins in bacterial cells are shorter time to express proteins coupled with lower costs for production of them. The proteins may be produced in bacterial cells either intracellularly as soluble proteins or inclusion bodies, or extracellularly by secretion into periplasm or nutrient media. Despite the wide applications in production of different types of recombinant proteins, the bacterial production of heterologous proteins continues to face major challenges pertaining to low yields or expression of the recombinant protein like Insulin, Granulocyte Colony Stimulating Factor (GCSF) etc.

There have been attempt in designing expression constructs or plasmid vectors that increase the expression of recombinant gene introduced in them. From the various strategies of increasing expression of recombinant gene in a host cell by way of increasing production of inclusion bodies include incorporating active promoters, optimising codons, including leader sequences or a combination of these and other strategies known in the art.

The inclusion of leader peptides in an expression construct finds favour since it directly leads to increase in production of inclusion bodies and may be attached to a purification or expression sequence tag for simplifying purification of recombinant protein during downstream processing. Further, the leader peptide may be cleaved using enzymatic methods.

Currently available leader peptides come with host of difficulties. One of them being overall incompatibility with large number of recombinant proteins and being very specific to a particular protein. There are fewer universal leader peptides and expression constructs based on them.

Accordingly, there is a need to develop expression constructs that are substantially universal in application with respect to expression of recombinant proteins in prokaryotic host cells and provide uniformly high expression for range of recombinant proteins of therapeutic and non-therapeutic value.

SUMMARY OF THE INVENTION

In view of the foregoing, the embodiments herein, provide an expression vector having a leader peptide sequence that results in higher production of inclusion bodies.

In an aspect, an expression vector for production of a recombinant protein in a host cell is provided. The expression vector includes a nucleotide sequence of Sequence ID No 2 encoding for a leader peptide of sequence ID No 3.

The expression vector expresses said recombinant protein as a fusion protein comprising fusion of said leader peptide of SEQ ID NO 3 and said recombinant protein and the host cell is bacteria, preferably *E. coli*. The leader peptide has Methionine at N-terminus, followed by Glycine to impart stability to fusion of said recombinant protein and said leader peptide.

The expression vector further includes DNA sequence encoding for a cleavage site or Restriction Enzyme (RE) site ligated to DNA sequence of said leader peptide. The expression vector further includes a DNA sequence encoding a multiple cloning site (MCS) in upstream region of said leader peptide, a DNA sequence of said heterologous protein is cloned in said MCS; a DNA sequence encoding ribosome binding site (RBS) ligated to N-terminus of said leader peptide, a DNA sequence encoding a promoter or operator in the downstream of said ribosome binding site and DNA sequence encoding an antibiotic selection marker in upstream region of said promoter/operator sequence.

BRIEF DESCRIPTION OF THE DRAWINGS

For a more complete understanding of the embodiments herein, reference should now be made to the embodiments illustrated in greater detail in the accompanying drawings and described below by way of examples.

DETAILED DESCRIPTION OF THE INVENTION

As required, detailed embodiments are disclosed herein; however, it is to be understood that the disclosed embodiments are merely exemplary, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language).

Vector Deposition

The vector pBGBactX is deposited for the patent purposes under Budapest Treaty at the MTCC (Microbial Type of Culture Collection) Chandigarh, India. The deposit was made on Mar. 21, 2013 and accorded deposit number as MTCC 5818. The sequence was characterised using DNA Sequencer.

As mentioned, there is a need for universal plasmid vectors which lead to high yield of heterologous proteins through simple purification processes. The embodiments herein provide a plasmid vector having nucleotide sequence listed under SEQ ID NO. 1.

Figure 1:
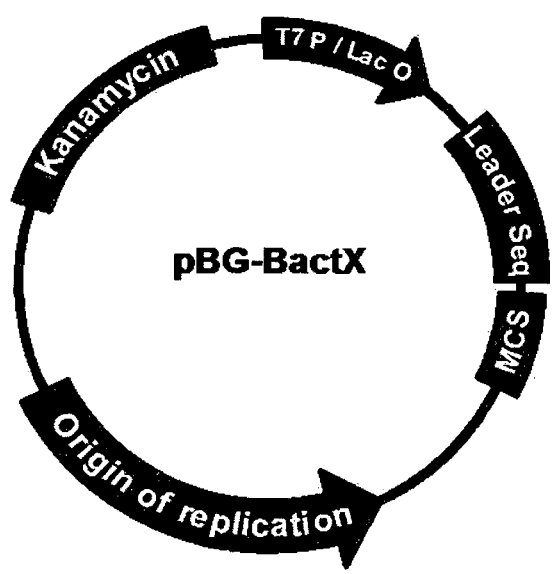
FIG. 1 illustrates an expression construct according to an embodiment herein.

The expression construct of FIG. 1 includes a DNA sequence, of SEQ ID NO 2 encoding for the leader peptide of SEQ ID NO. 3. The leader peptide of SEQ ID NO. 2 includes DNA sequence encoding for Methionine in its N-terminal end. The DNA sequence for Methionine is followed up by addition of DNA sequence encoding for Glycine. The addition of Glycine provides stability to the protein-leader peptide fusion.

The leader peptide of SEQ ID NO 2 is a neutral peptide with nearly as many hydrophobic amino acids as hydrophilic amino acids. In one embodiment, the leader peptide has 49% amino acids as hydrophobic. The neutrality of the leader peptide enables formation of stable inclusion bodies when the expression construct of FIG. 1 is expressed in the bacterial cells.

The DNA sequence for the protein of interest is inserted in the Multiple Cloning Site (MCS) of the expression vector as shown in FIG. 1. Multiple cloning site or polylinker constitutes a short segment of DNA which contains a number of (generally up to 20) Restriction Enzyme (RE) sites—a standard feature of engineered plasmids.

In a preferred embodiment, the leader peptide and the MCS are custom synthesised as single stranded oligonucleotides, which are used for synthesis of double stranded DNA fragment by PCR. In one embodiment, the overlapping PCR method is used to synthesise double stranded DNA. Optionally, the leader peptide and the MCS may be directly synthesised as double stranded DNA fragments.

Further, the RE sites were incorporated at 5' end and the 3' end of the synthesised DNA fragment. Furthermore, a Promoter/Operator region, a Ribosome Binding Site (RBS), an origin of replication and a antibiotic resistant gene were ligated with the PCR amplified DNA sequence coding for leader peptide, followed by MCS containing unique restriction enzyme sites. In one embodiment, the leader peptide is cloned downstream of the RBS, between Nco1 and EcoR1 restriction sites in the MCS.

The protein of interest may include filgrastim, interferon, human growth hormone, trypsin, carboxypeptidase, transferrin and various such recombinant proteins and peptides of therapeutic and non-therapeutic significance. A cleavage site may be included between the leader peptide and the protein of interest to cleave off the leader peptide and purify recombinant protein from the inclusion bodies. The expression vector of the embodiments herein has a sequence of SEQ ID No 1. The gene of interest may be inserted in any of the cleavage sites in the MCS.

The embodiments above are further explained through way of examples as follows:

EXAMPLES

Example 1: Construction of Vector

The nucleotide sequence coding the leader peptide and the multiple cloning sites (MCS) were custom synthesized as single stranded oligonucleotides. The single stranded oligonucleotides were utilized for the synthesis of double stranded DNA fragment by overlapping PCR method. The restriction enzyme (RE) sites were incorporated at 5' end and 3' end of the synthesized DNA fragment. The Promoter/Operator region, Ribosome binding site (RBS), origin of replication and antibiotic resistant gene were cleaved and ligated with the PCR amplified leader peptide sequence in MCS region containing unique restriction enzyme sites. The DNA fragment was cloned downstream of RBS between the Nco I and Xho I restriction site. Thereafter, the positive clones were screened by PCR method and the nucleotide sequence of the cloned Leader sequence and MCS were confirmed by DNA sequencing for the correctness of nucleotides. The construction of vector employs standard techniques, reagents and/or kits.

Figure 2A:
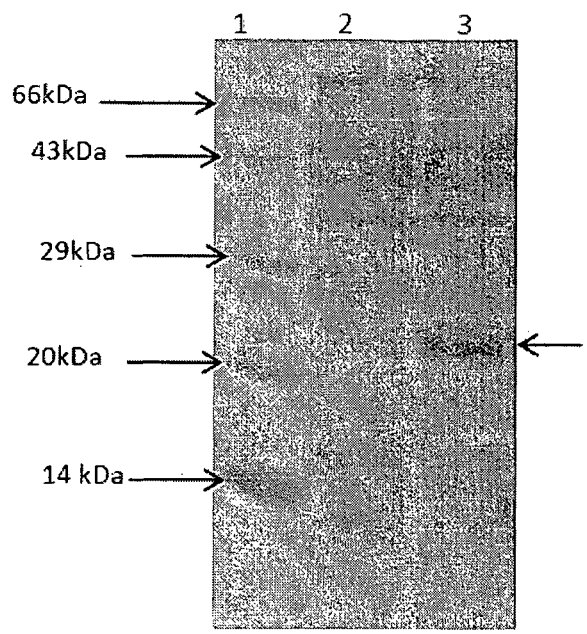
FIGS. 2a and 2b illustrates comparison of SDS PAGE analysis and densitometry data of GCSF as expressed in the expression vector of FIG. 1 and as expressed in a control vector.
Figure 2B:
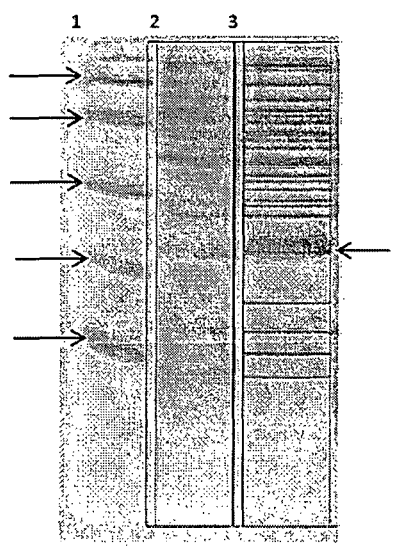

Example 2: SDS PAGE Analysis of GCSF Expressed from the Vector Described Herein The sequence encoding for GCSF was incorporated in the MCS of the expression vector described herein along with in a control vector devoid of any leader sequence. In the vector described herein, an enzymatic site for Enterokinase is inserted between the leader sequence and the GCSF sequence. The expression vector was cloned in bacterial cells and the GCSF inclusion bodies were obtained. The leader peptide was cleaved off by enzymatic and/or chemical means and the expression of GCSF from both the vectors was analysed on SDS PAGE as shown in FIG. 2a. Lane 1 shows Medium molecule weight marker, Lane 2 shows expression sample GCSF from control vector, Lane 3 shows GCSF expression sample from pBG-BactX vector. As may be observed, there is negligible expression of GCSF from the control vector. FIG. 2b illustrates gel densitometry data comparison for expression of GCSF in control vector and in the vector as described herein. Lane 1 shows Medium molecule weight marker, Lane 2 shows densitometry data for GCSF expression in the control vector and Lane 3 shows densitometry data for GCSF expression in the vector as described herein.

Example 3: Comparison of Expression Levels of GCSF by MALDI TOF Analysis

Figures 3A, 3B:
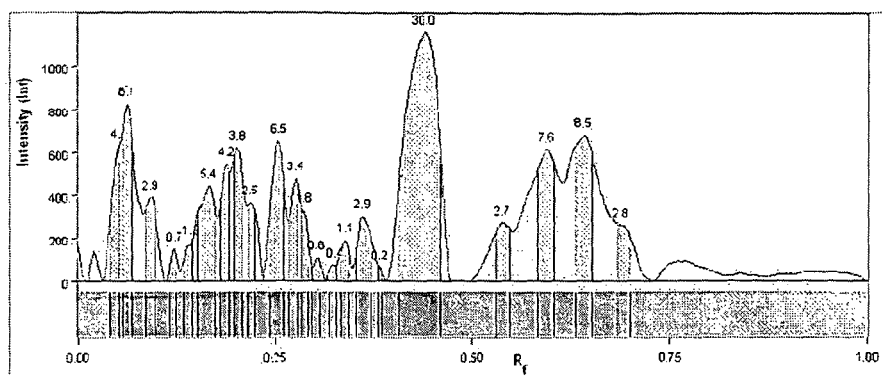
FIGS. 3a and 3b illustrates comparison of GCSF expression, as measured by MALDI-TOF, in a control vector and in vector of FIG. 1.

FIGS. 3a and 3b illustrates comparison of GCSF expression in a control vector with GCSF expression in vector of FIG. 1, according to an embodiment herein. The expression level in control vector is negligible whereas the expression level in the vector described herein has expression level of 30%.

We claim:

1. An expression vector for production of a recombinant protein in a host cell comprising a nucleotide sequence of SEQ ID NO:2 encoding for a leader peptide of SEQ ID NO:3.

2. The expression vector of claim 1, wherein said expression vector expresses said recombinant protein as a fusion protein comprising fusion of said leader peptide of SEQ ID NO:3 and said recombinant protein.

3. The expression vector of claim 1, wherein said host cell is *E. coli*.

4. The expression vector of claim 1 further comprising a DNA sequence encoding for a cleavage site or Restriction Enzyme (RE) site ligated to the DNA sequence of said leader peptide.

5. The expression vector of claim 1 further comprising a DNA sequence encoding a multiple cloning site (MCS) in upstream region of said leader peptide, a DNA sequence of said recombinant protein is cloned in said MCS, a DNA sequence encoding a ribosome binding site (RBS) ligated to N-terminus of said leader peptide, a DNA sequence encoding a promoter or operator in the downstream of said ribosome binding site and a DNA sequence encoding an antibiotic selection marker in upstream region of said promoter/operator sequence.

6. The expression vector of claim 5, wherein said antibiotic selection marker is kanamycin.

7. A process for production of recombinant proteins comprising expressing said recombinant protein in a host cell using said expression vector of claim 1, wherein the expression vector has a sequence of SEQ ID NO:1.

8. A process for production of recombinant proteins comprising expressing said recombinant protein in a host cell using said expression vector of claim 1, wherein said expression vector further comprises a nucleotide sequence encoding for Granulocyte Colony Stimulating Factor (GCSF), wherein said nucleotide sequence encoding for GCSF is separated from said leader peptide by an enterokinase cleavage site.

* * * * *

SEQUENCE LISTING

```
<160> NUMBER OF SEQ ID NOS: 3

<210> SEQ ID NO 1
<211> LENGTH: 5439
<212> TYPE: DNA
<213> ORGANISM: Escherichia coli
```

-continued

```
<400> SEQUENCE: 1
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggc tccctttagg       180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggatttt tgccgattc ggcctattgg ttaaaaaatg agctgattta       420
acaaaatttt aacgcgaatt ttaacaaaat attaacgttt acaatttcag gtggcacttt     480
tcggggaaat gtgcgcggaa cccctatttg tttattttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttc cctcgtcaaa ataaggtta tcaagtgaga      780 aatcaccatg agtgacgact gaatccggtg agaatggcaa agtttatgc atttctttcc     840 agacttgttc aacaggccag ccattacgct cgtcatcaaa atcactcgca tcaaccaaac     900
cgttattcat tcgtgattgc gcctgagcga acgaaatac gcgatcgctg ttaaaaggac      960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccattata cccatataaa tcagcatcca    1320
tgttggaatt taatcgcggc ctagagcaag acgtttccg ttgaatatgg ctcataacac     1380
cccttgtatt actgtttatg taagcagaca gttttattgt tcatgaccaa atcccttaa    1440 cgtgagtttt cgttccactg agcgtcagac cccgtagaaa agatcaaagg atcttcttga    1500 gatcctttt ttctgcgcgt aatctgctgc ttgcaaacaa aaaaaccacc gctaccagcg     1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccggttg gactcaagac gatagttacc ggataaggcg     1800
cagcggtcgg gctgaacggg gggttcgtgc acacagccca gcttggagcg aacgacctac    1860
accgaactga tacctaca gcgtgagcta tgagaaagcg ccacgcttcc cgaagggaga     1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280 tatttttctcc ttacgcatct gtgcggtatt tcacaccgca tatatggtgc actctcagta    2340
```

```
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg gggtaatga taccgatgaa    2760 acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccgaaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
```

-continued

```
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatatacc atgggcagca gcatgggcgc tactggtgtg    5100
ccgttcagcg gaatggtgag cctccagatg ggtcatcaag gaagcggtag ctcccatcat    5160
catcatcatc acgaattcgg atccgagctc cgtcgacttc gaaggtaccc ctgcaggcct    5220
aggaccggtc aattgcttaa gactagtgac gtcttaatta aaagcttgcg gccgcactcg    5280
agcaccacca ccaccaccac tgagatccgg ctgctaacaa agcccgaaag gaagctgagt    5340
tggctgctgc caccgctgag caataactag cataacccct tggggcctct aaacgggtct    5400 tgagggggttt tttgctgaaa ggaggaacta tatccggat                          5439
```

```
<210> SEQ ID NO 2
<211> LENGTH: 84
<212> TYPE: DNA
<213> ORGANISM: Artificial Sequence
<220> FEATURE:
<223> OTHER INFORMATION: Leader peptide nucleotide sequence

<400> SEQUENCE: 2
atgggcagca gcatgggcgc tactggtgtg ccgttcagcg gaatggtgag cctccagatg    60
ggtcatcaag gaagcggtag ctcc                                           84

<210> SEQ ID NO 3
<211> LENGTH: 28
<212> TYPE: PRT
<213> ORGANISM: Artificial Sequence
<220> FEATURE:
<223> OTHER INFORMATION: Leader peptide

<400> SEQUENCE: 3

Met Gly Ser Ser Met Gly Ala Thr Gly Val Pro Phe Ser Gly Met Val
1               5                   10                  15

Ser Leu Gln Met Gly His Gln Gly Ser Gly Ser Ser
            20                  25
```